(12) United States Patent
Welford et al.

(10) Patent No.: US 9,383,263 B2
(45) Date of Patent: Jul. 5, 2016

(54) SYSTEMS AND METHODS FOR NARROWING A WAVELENGTH EMISSION OF LIGHT

(71) Applicant: VOLCANO CORPORATION, San Diego, CA (US)

(72) Inventors: David Welford, Danvers, MA (US); Badr Elmaanaoui, Billerica, MA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 14/108,893

(22) Filed: Dec. 17, 2013

(65) Prior Publication Data

US 2014/0177237 A1 Jun. 26, 2014

Related U.S. Application Data

(60) Provisional application No. 61/745,270, filed on Dec. 21, 2012.

(51) Int. Cl.
| | | |
|---|---|---|
| *A61B 5/00* | (2006.01) | |
| *G01B 9/02* | (2006.01) | |
| *G01J 9/02* | (2006.01) | |
| *H01S 3/067* | (2006.01) | |

(52) U.S. Cl.
CPC ............ *G01J 9/0246* (2013.01); *A61B 5/0066* (2013.01); *A61B 5/0073* (2013.01); *G01B 9/02091* (2013.01); *G01J 2009/0226* (2013.01); *H01S 3/06791* (2013.01)

(58) Field of Classification Search
CPC . H01S 3/0078; H01S 3/06791; H01S 3/1003; A61B 5/0066; A61B 5/0073; G01B 9/02091
See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

Sihan et al., 2008, A novel approach to quantitative analysis of intraluminal optical coherence tomography imaging, Comput. Cardiol:1089-1092.

(Continued)

*Primary Examiner* — Eric Bolda
(74) *Attorney, Agent, or Firm* — Brown Rudnick LLP; Thomas C. Meyers

(57) ABSTRACT

The present invention generally relates to methods and systems for narrowing a wavelength emission of light. In certain aspects, methods of the invention involve transmitting light through a filter and passing a portion of the filtered light through a gain chip assembly at least two times before that portion of light passes again through the filter.

9 Claims, 7 Drawing Sheets

(56) References Cited

U.S. PATENT DOCUMENTS

| | | |
|---|---|---|
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |

(56) References Cited

U.S. PATENT DOCUMENTS

| | | |
|---|---|---|
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,577,789 B1 * | 6/2003 | Wang ............................... 385/27 |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,678,087 B1 * | 1/2004 | Masuda et al. ................ 359/334 |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |

(56) References Cited

U.S. PATENT DOCUMENTS

| | | |
|---|---|---|
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B2 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |

(56) References Cited

U.S. PATENT DOCUMENTS

| | | |
|---|---|---|
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |

(56) References Cited

U.S. PATENT DOCUMENTS

| | | |
|---|---|---|
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0024066 A1* | 2/2006 | Fujiwara et al. ............... 398/183 |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241492 A1* | 10/2006 | Boese .................. A61B 5/6852 600/473 |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201127 A1* | 8/2007 | Maeda ........................ 359/344 |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |

(56) References Cited

U.S. PATENT DOCUMENTS

| | | |
|---|---|---|
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0021724 A1* | 1/2009 | Mahadevan-Jansen  A61B 5/0066 356/73 |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0097614 A1* | 4/2010 | Kourogi et al. ............... 356/477 |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0051143 A1* | 3/2011 | Flanders et al. ............... 356/451 |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0157686 A1* | 6/2011 | Huber et al. .................. 359/333 |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |

(56) References Cited

U.S. PATENT DOCUMENTS

| | | |
|---|---|---|
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |

(56) References Cited

FOREIGN PATENT DOCUMENTS

| | | |
|---|---|---|
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferonnetry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60 (9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent, 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radiofrequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12 (24):6033-6039.
Zitova et al., 2003, Image registration methods: A survey. Image and Vision Computing, 21(11):977-1000.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.

(56) References Cited

OTHER PUBLICATIONS

Miller et al., 2010, The MILLER banding procedure is an effective method for treating dialysis-associated steal syndrome, Kidney International 77:359-366.

Milstein et al., 1983, Hybrid hybridomas and their use in immunohistochemistry, Nature 305:537-540.

Mindlin et al., 1936, A force at a point of a semi-infinite solid, Physics, 7:195-202.

Morrison et al., 1984, Chimeric human antibody molecules: mouse antigen-binding domains with human constant region domains, PNAS 81:6851-6855.

Munson et al., 1980, Ligand: a versatile computerized approach for characterization of ligand-binding systems, Analytical Biochemistry, 107:220-239.

Nezam, 2008, High Speed Polygon-Scanner-Based Wavelength-Swept Laser Source in the Telescope-Less Configurations with Application in Optical Coherence Tomography, Optics Letters 33(15):1741-1743.

Nissen, 2001, Coronary Angiography and Intravascular Ultrasound, American Journal of Cardiology, 87 (suppl):15A-20A.

Nitenberg et al., 1995, Coronary vascular reserve in humans: a critical review of methods of evaluation and of interpretation of the results, Eur Heart J. 16(Suppl 1):7-21.

Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filed May 7, 2009, of the same title, published on Nov. 12, 2009, as WO 2009/137704, and accompanying English translation of the Notice of Reason(s) for Refusal and machine translations of JP11-56786 and JP2004-290548 (56 pages).

Nygren, 1982, Conjugation of horseradish peroxidase to Fab fragments with different homobifunctional and heterobifunctional cross-linking reagents. A comparative study, J. Histochem. and Cytochem. 30:407-412.

Oesterle et al., 1986, Angioplasty at coronary bifurcations: single-guide, two-wire technique, Cathet Cardiovasc Diagn., 12:57-63.

Okuno et al., 2003, Recent Advances in Optical Switches Using Silica-based PLC Technology, NTT Technical Review 1(7):20-30.

Oldenburg et al., 1998, Nanoengineering of Optical Resonances, Chemical Physics Letters 288:243-247.

Oldenburg et al., 2003, Fast-Fourier-Domain Delay Line for In Vivo Optical Coherence Tomography with a Polygonal Scanner, Applied Optics, 42(22):4606-4611.

Othonos, 1997, Fiber Bragg gratings, Review of Scientific Instruments 68(12):4309-4341.

Owens et al., 2007, A Survey of General-Purpose Computation on Graphics Hardware, Computer Graphics Forum 26 (1):80-113.

Pain et al., 1981, Preparation of protein A-peroxidase mono conjugate using a heterobifunctional reagent, and its use in enzyme immunoassays, J Immunol Methods, 40:219-30.

Park et al., 2005, Real-time fiber-based multi-functional spectral-domain optical coherence tomography at 1.3 um., Optics Express 13(11):3931-3944.

Pasquesi et al., 2006, In vivo detection of exercise induced ultrastructural changes in genetically-altered murine skeletal muscle using polarization-sensitive optical coherence tomography, Optics Express 14(4)1 547-1556.

Pepe et al., 2004, Limitations of the odds ratio in gauging the performance of a diagnostic, prognostic, or screening marker, American Journal of Epidemiology 159(9):882-890.

Persson et al., 1985, Acoustic impedance matching of medical ultrasound transducers, Ultrasonics, 23(2):83-89.

Placht et al., 2012, Fast time-of-flight camera based surface registration for radiotherapy patient positioning, Medical Physics 39(1):4-17.

Rabbani et al., 1999, Review: Strategies to achieve coronary arterial plaque stabilization, Cardiovascular Research 41:402-417.

Radvany et al., 2008, Plaque Excision in Management of Lower Extremity Peripheral Arterial Disease with the SilverHawk Atherectomy Catheter, Seminars in Interventional Radiology, 25(1):11-19.

Reddy et al., 1996, An FFT-Based Technique for Translation, Rotation, and Scale-Invariant Image Registration, IEEE Transaction on Image Processing 5(8):1266-1271.

Riechmann et al., 1988, Reshaping human antibodies for therapy, Nature, 332:323-327.

Rivers et al., 1992, Correction of steal syndrome secondary to hemodialysis access fistulas: a simplified quantitative technique, Surgery, 112(3):593-7.

Robbin et al., 2002, Hemodialysis Arteriovenous Fistula Maturity: US Evaluation, Radiology 225:59-64.

Rollins et al., 1998, In vivo video rate optical coherence tomography, Optics Express 3:219-229.

Sarunic et al., 2005, Instantaneous Complex Conjugate Resolved Spectral Domain and Swept-Source OCT Using 3x3 Fiber Couplers, Optics Express 13(3):957-967.

Satiani et al., 2009, Predicted Shortage of Vascular Surgeons in the United States, J. Vascular Surgery 50:946-952.

Schneider et al., 2006, T-banding: A technique for flow reduction of a hyper-functioning arteriovenous fistula, J Vasc Surg. 43(2):402-405.

Sen et al., 2012, Development and validation of a new adenosine-independent index of stenosis severity from coronary wave-intensity analysis, Journal of the American College of Cardiology 59(15):1392-1402.

Setta et al., 2005, Soft versus firm embryo transfer catheters for assisted reproduction: a systematic review and meta-analysis, Human Reproduction, 20(11):3114-3121.

Seward et al., 1996, Ultrasound Cardioscopy: Embarking on New Journey, Mayo Clinic Proceedings 71(7):629-635.

Shen et al., 2006, Eigengene-based linear discriminant model for tumor classification using gene expression microarray data, Bioinformatics 22(21):2635-2642.

Abdi et al., 2010, Principal component analysis, Wiley Interdisciplinary Reviews: Computational Statistics 2:433-459.

Adler et al., 2007, Phase-Sensitive Optical Coherence Tomography at up to 370,000 Lines Per Second Using Buffered Fourier Domain Mode-Locked Lasers, Optics Letters, 32(6):626-628.

Agresti, 1996, Models for Matched Pairs, Chapter 8, An Introduction to Categorical Data Analysis, Wiley-Interscience A John Wiley & Sons, Inc., Publication, Hoboken, New Jersey.

Akasheh et al., 2004, Development of piezoelectric micromachined ultrasonic transducers, Sensors and Actuators A Physical, 111:275-287.

Amini et al., 1990, Using dynamic programming for solving variational problems in vision, IEEE Transactions on Pattern Analysis and Machine Intelligence, 12(9):855-867.

Bail et al., 1996, Optical coherence tomography with the "Spectral Radar"—Fast optical analysis in volume scatterers by short coherence interferometry, Optics Letters 21(14):1087-1089.

Bain, 2011, Privacy protection and face recognition, Chapter 3, Handbook of Face Recognition, Stan et al., Springer-Verlag.

Barnea et al., 1972, A class of algorithms for fast digital image registration, IEEE Trans. Computers, 21(2):179-186.

Blanchet et al., 1993, Laser Ablation and the Production of Polymer Films, Science, 262(5134):719-721.

Bonnema, 2008, Imaging Tissue Engineered Blood Vessel Mimics with Optical Tomography, College of Optical Sciences dissertation, University of Arizona (252 pages).

Bouma et al., 1999, Power-efficient nonreciprocal interferometer and linear-scanning fiber-optic catheter for optical coherence tomography, Optics Letters, 24(8):531-533.

Breiman, 2001, Random forests, Machine Learning 45:5-32.

Brown, 1992, A survey of image registration techniques, ACM Computing Surveys 24(4):325-376.

Bruining et al., 2009, Intravascular Ultrasound Registration/Integration with Coronary Angiography, Cardiology Clinics, 27(3):531-540.

(56) References Cited

OTHER PUBLICATIONS

Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61 (1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).
International Search Report and Written Opinion mailed Nov. 2, 2012, for International Patent Application No. PCT/US12/53168, filed Aug. 30, 2013 (8 pages).
International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).
International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).
International Search Report and Written Opinion mailed on Feb. 28, 2014, for International Patent Application No. PCT/US13/75990, filed Dec. 18, 2013 (7 pages).
International Search Report and Written Opinion mailed on Jan. 16, 2009, for International Patent Application No. PCT/US08/78963 filed on Oct. 6, 2008 (7 pages).
International Search Report and Written Opinion mailed on Jul. 30, 2014, for International Patent Application No. PCT/US14/21659, filed Mar. 7, 2014 (15 pages).
International Search Report and Written Opinion mailed on Mar. 10, 2014, for International Patent Application No. PCT/US2013/076212, filed Dec. 18, 2013 (8 pages).

(56) References Cited

OTHER PUBLICATIONS

International Search Report and Written Opinion mailed on Mar. 11, 2014, for International Patent Application No. PCT/US13/76173, filed Dec. 16, 2013 (9 pages).

International Search Report and Written Opinion mailed on Mar. 11, 2014, for International Patent Application No. PCT/US13/76449, filed Dec. 19, 2013 (9 pages).

International Search Report and Written Opinion mailed on Mar. 18, 2014, for International Patent Application No. PCT/US2013/076502, filed Dec. 19, 2013 (7 pages).

International Search Report and Written Opinion mailed on Mar. 18, 2014, for International Patent Application No. PCT/US2013/076788, filed Dec. 20, 2013 (7 pages).

International Search Report and Written Opinion mailed on Mar. 19, 2014, for International Patent Application No. PCT/US13/75349, filed Dec. 16, 2013 (10 pages).

International Search Report and Written Opinion mailed on Mar. 19, 2014, for International Patent Application No. PCT/US2013/076587, filed Dec. 19, 2013 (10 pages).

International Search Report and Written Opinion mailed on Mar. 19, 2014, for International Patent Application No. PCT/US2013/076909, filed Dec. 20, 2013 (7 pages).

International Search Report and Written Opinion mailed on Mar. 7, 2014, for International Patent Application No. PCT/US2013/076304, filed Dec. 18, 2013 (9 pages).

International Search Report and Written Opinion mailed on Mar. 7, 2014, for International Patent Application No. PCT/US2013/076480, filed Dec. 19, 2013 (8 pages).

International Search Report and Written Opinion mailed on Mar. 7, 2014, for International Patent Application No. PCT/US2013/076512, filed Dec. 19, 2013 (8 pages).

International Search Report and Written Opinion mailed on Mar. 7, 2014, for International Patent Application No. PCT/US2013/076531, filed Dec. 19, 2013 (10 pages).

Jakobovits et al., 1993, Analysis of homozygous mutant chimeric mice:deletion of the immunoglobulin heavy-chain joining region blocks B-cell development and antibody production, PNAS USA 90:2551-255.

Jakobovits et al., 1993, Germ-line transmission and expression of a human-derived yeast artificial chromosome, Nature 362:255-258.

Jang et al., 2002, Visualization of Coronary Atherosclerotic Plaques in Patients Using Optical Coherence Tomography: Comparison With Intravascular Ultrasound, Journal of the American College of Cardiology 39:604-609.

Jiang et al., 1992, Image registration of multimodality 3-D medical images by chamfer matching, Proc. SPIE 1660, Biomedical Image Processing and Three-Dimensional Microscopy, 356-366.

Johnson et al., 1993, Human antibody engineering: Current Opinion in Structural Biology, 3:564-571.

Jones et al., 1986, Replacing the complementarity-determining regions in a human antibody with those from a mouse, Nature, 321:522-525.

Juviler et al., 2008, Anorectal sepsis and fistula-in-ano, Surgical Technology International, 17:139-149.

Karapatis et al., 1998, Direct rapid tooling:a review of current research, Rapid Prototyping Journal, 4(2):77-89.

Karp et al., 2009, The benefit of time-of-flight in PET imaging, J Nucl Med 49:462-470.

Kelly et al., 2005, Detection of Vascular Adhesion Molecule-1 Expression Using a Novel Multimodal Nanoparticle, Circulation Research 96:327-336.

Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.

Kersey et al., 1991, Polarization insensitive fiber optic Michelson interferometer, Electron. Lett. 27:518-520.

Kheir et al., 2012, Oxygen Gas-Filled Microparticles Provide Intravenous Oxygen Delivery, Science Translational Medicine 4(140):140ra88 (10 pages).

Khuri-Yakub et al., 2011, Capacitive micromachined ultrasonic transducers for medical imaging and therapy, J Micromech Microeng. 21(5):054004-054014.

Kirkman, 1991, Technique for flow reduction in dialysis access fistulas, Surg Gyn Obstet, 172(3):231-3.

Kohler et al., 1975, Continuous cultures of fused cells secreting antibody of predefined specificity, Nature, 256:495-7.

Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.

Kozbor et al., 1984, A human hybrid myeloma for production of human monoclonal antibodies, J. Immunol., 133:3001-3005.

Kruth et al., 2003, Lasers and materials in selective laser sintering, Assembly Automation, 23(4):357-371.

Kumagai et al., 1994, Ablation of polymer films by a femtosecond high-peak-power Ti:sapphire laser at 798 nm, Applied Physics Letters, 65(14):1850-1852.

Larin et al., 2002, Noninvasive Blood Glucose Monitoring with Optical Coherence Tomography: a pilot study in human subjects, Diabetes Care, 25(12):2263-7.

Larin et al., 2004, Measurement of Refractive Index Variation of Physiological Analytes using Differential Phase OCT, Proc of SPIE 5325:31-34.

Laufer, 1996, Introduction to Optics and Lasers in Engineering, Cambridge University Press, Cambridge UK:156-162.

Lefevre et al., 2001, Stenting of bifurcation lesions:a rational approach, J. Interv. Cardiol., 14(6):573-585.

Li et al., 2000, Optical Coherence Tomography: Advanced Technology for the Endoscopic Imaging of Barrett's Esophagus, Endoscopy, 32(12):921-930.

International Search Report and Written Opinion mailed on Apr. 16, 2014, for International Patent Application No. PCT/US2013/075636, filed Dec. 17, 2013 (8 pages).

\* cited by examiner

SYSTEMS AND METHODS FOR NARROWING A WAVELENGTH EMISSION OF LIGHT

RELATED APPLICATION

This application claims the benefit of and priority to U.S. Provisional Application Ser. No. 61/745,270, filed Dec. 21, 2012, which is incorporated by reference in its entirety.

FIELD OF THE INVENTION

The present invention generally relates to methods and systems for narrowing a wavelength emission of light.

BACKGROUND

Optical coherence tomography (OCT) is an established medical imaging technique that relies on light for producing an image. In OCT, light from a broadband light source is split by an optical fiber splitter with one fiber directing light to a sample path and the other fiber directing light to a reference path mirror. An end of the sample path is typically connected to a scanning device. The light reflected from the scanning device is recombined with the signal from the reference mirror to form interference fringes, which are transformed into a depth resolved image.

Numerous different OCT techniques have been developed, including swept source OCT. In swept source OCT, a narrowband light source is rapidly tuned over a broad optical bandwidth, and spectral components are encoded in time. Thus, image quality in swept source OCT relies on the swept laser source achieving very narrow bandwidths at very high frequencies (e.g., 20-200 kHz) over a very short period of time (e.g., 10,000-10,000,000 Sweeps/sec).

A typical set-up for a swept source OCT system uses a ring resonator that includes an optical amplifier, a tunable filter, and an optical coupler. Laser light at a specific bandwidth is produced by the optical amplifier and sent through the filter. The filter assists in maintaining the outputted light at the specific bandwidth. From the filter, the light travels to the optical coupler where a portion of the light is directed to an interferometer and the remainder of the light returns to the optical amplifier. The process repeats to achieve different bandwidths of light.

A problem with this set-up is that a single pass through an optical amplifier cannot impart enough energy to the light to obtain the very narrow bandwidths in an optimal amount of time. Another problem with this set-up is that a single pass through an optical amplifier cannot impart enough energy to the light to prevent broadening of the obtained bandwidth, particularly at higher frequencies. Both problems lead to degradation of image quality.

SUMMARY

The invention provides a ring resonator set-up for optical coherence tomography (OCT) in which light passes through an optical amplifier twice before it proceeds to an OCT interferometer. As encompassed by the invention, a first pass of light exiting the optical amplifier is directed back through the amplifier rather than continuing through the ring resonator. Light exiting the amplifier can be sent back through the amplifier by using, for example, a mirror. The light re-enters the amplifier, wherein it is amplified a second time. This re-amplified light is then transmitted through the ring resonator where it can continue onto the OCT interferometer. An optical coupler may be used to coordinate the passage of light between the amplifier and the rest of the ring resonator. The provided ring resonators may also include a filter for maintaining the narrow bandwidth of light after it has been amplified twice by the optical amplifier.

By passing the light through the amplifier twice during a single trip through the resonator, a narrowed bandwidth of light is achieved faster than only passing the light through an interferometer once before proceeding to the interferometer. The second pass through the amplifier in a single trip also imparts additional energy to the light, which prevents undesired broadening of the obtained bandwidth at higher frequencies. Accordingly, the provided ring resonators are able to produce high quality OCT images that avoid the image degradation problems associated with prior art ring resonator configurations.

The provided ring resonator can serve as a light source for a variety of applications, including medical imaging. For example, light leaving the ring resonator can be directed towards an OCT system. As noted above, the present invention is particularly suited for OCT due to the improvement of image quality.

In addition to the provided resonators, the invention also encompasses methods for narrowing a wavelength of light. The methods involve passing light through an optical amplifier of a ring resonator twice during one pass around the ring resonator. Using the provided methods, a narrow bandwidth of light is achieved in an optimal amount of time and image quality is improved.

DETAILED DESCRIPTION

Figure 1:
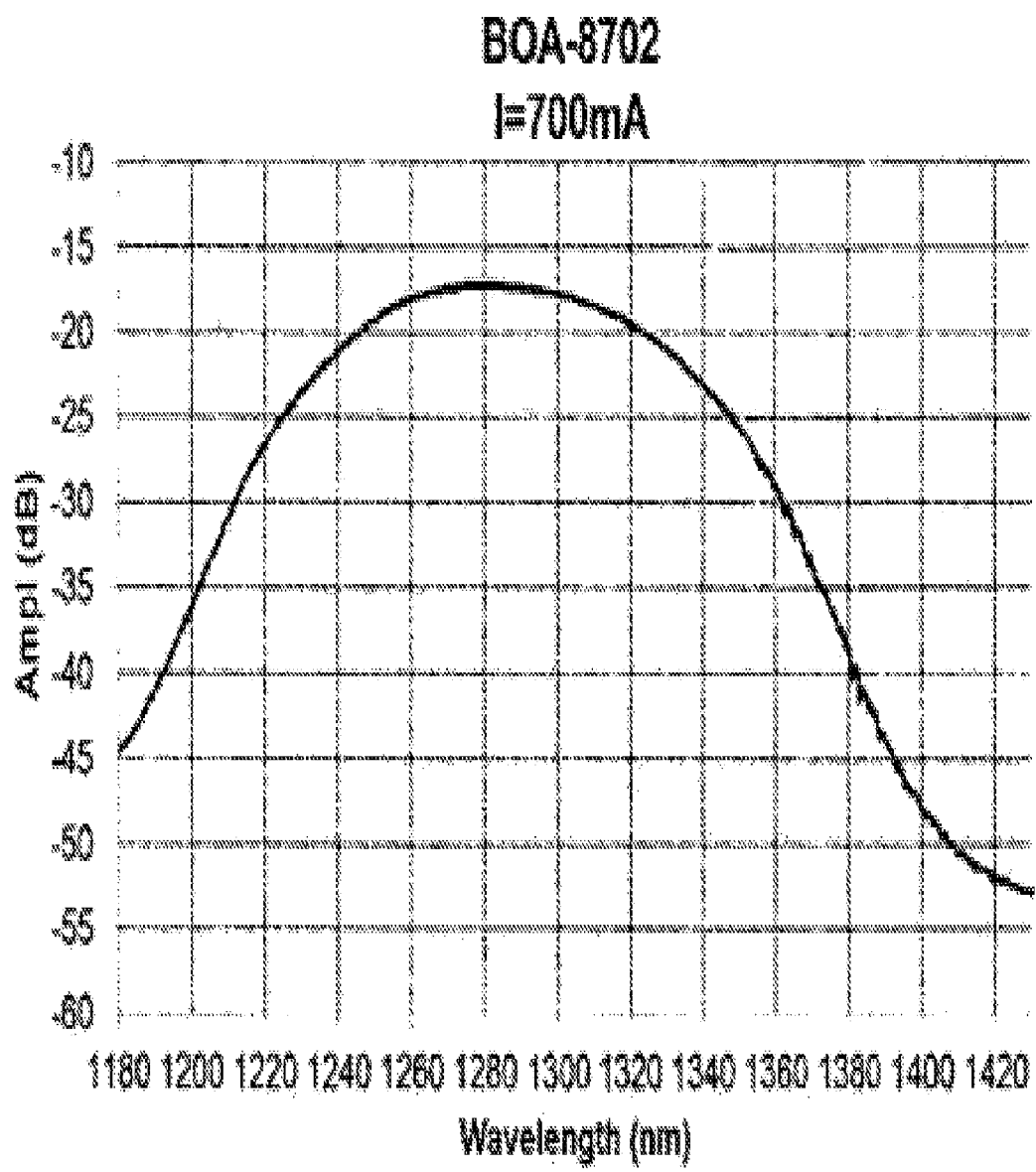
FIG. 1 is a gain curve for a booster optical amplifier.

The invention generally relates to methods and systems for producing narrow emissions of light. The invention can involve transmitting light through a filter and passing a portion of the filtered light through a gain chip assembly at least two times before that portion of the filtered light passes again through the filter. Broadband light is emitted from a light source and transmitted through a filter. The filtered light is passed through a gain chip assembly in which the light signal is amplified. The amplified light leaves the gain chip assembly, whereupon a portion of that light is sent back into the gain chip assembly, where it is amplified a second time. This re-amplified light is then directed back through the filter, wherein the whole process can repeat itself. Accordingly, the re-amplification of filtered light prior to its return to the filter can include sending the light through a gain medium in the gain chip assembly back through the gain chip assembly. This results in a second pass through the assembly gain medium before passing again through the filter.

Any optical filter is useful for practicing the invention. As encompassed by the invention, the filter receives light from a broadband light source and emits light of a predetermined wavelength. An optical filter typically has a peak reflectivity and a background reflectivity. The peak reflectivity indicates an amount of light output (reflected) at the specified wavelength, wherein a desired wavelength can be set in a tunable filter by placing mirrors in an etalon at an appropriate distance apart. The background reflectivity indicates an amount of light output at wavelengths other than the desired wavelength.

Typical filters might have, for example, a 20% peak reflectivity and a 0.02% background reflectivity. The ratio of these numbers ($10^3$) defines the filter contrast ratio, expressed in decibels (dB) (here, 30 dB). Thus, if light of a certain wavelength, for example, 1200 nm, is intended, the filter will transmit light at 1200 nm as well as a broad spectrum of light at lower power in a ratio of 30 dB.

In some embodiments, systems of the invention include an optical filter that can be tuned to a desired wavelength, i.e., a tunable filter. Amplified light of a selected wavelength is obtained by tuning the filter to that wavelength and sending the light into the gain medium with sufficient input power to achieve a desired output power.

Where an optical system requires a particular wavelength of amplified light, the light source may include an optical filter module such as a tunable optical filter in optical communication with a gain component.

In certain embodiments of the invention, the tunable filter is a voltage-controlled optical attenuator. In a VCOA, an optical attenuator is placed between an input and output lens for obstructing the path of an incoming light beam. The attenuator has variable attenuation (reflection, absorption, etc.) which is controlled for maintaining a preset power or wavelength of the outgoing light beam. To this end, a fraction of the outgoing signal is diverted to an output detector by reflecting off an end face of a lens, and processed for obtaining a control signal representative of the output power. An electric output displaces the attenuator to a position corresponding to a preset output power. Further detail on VCOAs can be found, for example, in U.S. Pat. No. 5,745,634, incorporated by reference herein in its entirety.

The invention also encompasses the use of a gain chip assembly that amplifies the power of light that is transmitted through it. As provided by the invention, light travels from the filter to the gain chip assembly for amplification. The gain chip assembly, or gain component, generally refers to any device known in the art capable of amplifying light such as an optical amplifier, laser, or any component employing a gain medium. A gain medium is a material that increases the power of light transmitted through the gain medium. Exemplary gain mediums include crystals (e.g., sapphire), doped crystals (e.g., yttrium aluminum garnet, yttrium orthovanadate), glasses such as silicate or phosphate glasses, gasses (e.g., mixtures of helium and neon, nitrogen, argon, or carbon monoxide), semiconductors (e.g., gallium arsenide, indium gallium arsenide), and liquids (e.g., rhodamine, fluorescein).

When light interacts with the material of the gain medium, several outcomes may be obtained. Light may be transmitted through the material unaffected or reflect off a surface of the material. Alternatively, an incident photon of light can exchange energy with an electron of an atom within the material by either absorption or stimulated emission. If the photon is absorbed, the electron transitions from an initial energy level to a higher energy level. In three-level system, there is a transient energy state associated with a third energy level.

When electron returns to ground state, a photon is emitted. When photons are emitted, there is a net increase in power of light within the gain medium. In stimulated emission, an electron emits energy $\Delta E$ through the creation of a photon of frequency $v_{12}$ and coherent with the incident photon. Two photons are coherent if they have the same phase, frequency, polarization, and direction of travel. Equation 1 gives the relationship between energy change $\Delta E$ and frequency $v_{12}$:

$$\Delta E = h v_{12} \quad (1)$$

where h is Plank's constant. Light produced this way can be temporally coherent, i.e., having a single location that exhibits clean sinusoidal oscillations over time.

An electron can also release a photon by spontaneous emission. Amplified spontaneous emission (ASA) in a gain medium produces spatially coherent light, e.g., having a fixed phase relationship across the profile of a light beam.

Emission prevails over absorption when light is transmitted through a material having more excited electrons than ground state electrons—a state known as a population inversion. A population inversion can be obtained by pumping in energy (e.g., current or light) from outside. Where emission prevails, the material exhibits a gain G defined by Equation 2:

$$G = 10 \, \text{Log}_{10}(P_{out}/P_{in}) \, \text{dB} \quad (2)$$

where $P_{out}$ and $P_{in}$ are the optical output and input power of the gain medium.

As encompassed by the invention, the gain chip component can be an optical amplifier or a laser. An optical amplifier is a device that amplifies an optical signal directly, without the need to first convert it to an electrical signal. An optical amplifier generally includes a gain medium (e.g., without an optical cavity), or one in which feedback from the cavity is suppressed. Exemplary optical amplifiers include doped fibers, bulk lasers, semiconductor optical amplifiers (SOAs) and Raman optical amplifiers. In doped fiber amplifiers and bulk lasers, stimulated emission in the amplifier's gain medium causes amplification of incoming light. In SOAs, electron-hole recombination occurs. In Raman amplifiers, Raman scattering of incoming light with phonons (i.e., excited state quasiparticles) in the lattice of the gain medium produces photons coherent with the incoming photons.

Doped fiber amplifiers (DFAs) are optical amplifiers that use a doped optical fiber as a gain medium to amplify an optical signal. In a DFA, the signal to be amplified and a pump laser are multiplexed into the doped fiber, and the signal is amplified through interation with the doping ions. The most common DFA is Erbium Doped Fiber Amplifier (EDFA), which features a silica fiber with an Erbium-ion doped core. An exemplary EDFA is the Cisco ONS 15501 EDFA from Cisco Systems, Inc. (San Jose, Calif.)

Semiconductor optical amplifiers (SOAs) are amplifiers that use a semiconductor to provide the gain medium. In a SOA, input light is transmitted through the gain medium and amplified output light is produced. An SOA includes n-cladding layer and p-cladding layer. The SOA also typically includes a group III-V compound semiconductor such as GaAs/AlGaAs, InP/InGas, InP/InGaAsP and InP/InAlGaAs, though any suitable semiconductor material may be used.

A typical semiconductor optical amplifier includes a double heterostructure material with n-type and p-type high band gap semiconductor layers around a low band gap semiconductor. The high band gap layers are sometimes referred to as p-cladding layers (which have more holes than electrons) and n-cladding layers (which have more electrons than holes). The carriers are injected into the gain medium where they recombine to produce photons by both spontaneous and stimulated emission. The cladding layers also function as waveguides to guide the propagation of the light signal. Semiconductor optical amplifiers are described in Dutta and Wang, Semiconductor Optical Amplifiers, World Scientific Publishing Co. Pte. Ltd., Hackensack, N.J. (2006) the contents of which are hereby incorporated by reference in their entirety.

Booster Optical Amplifiers (BOAs) are single-pass, traveling-wave amplifiers that only amplify one state of polarization generally used for applications where the input polarization of the light is known. Since a BOA is polarization sensitive, it can provide desirable gain, noise, bandwidth, and saturation power specification. In some embodiments, a BOA includes a semiconductor gain medium. The input and output of BOA can be coupled to one or more waveguides on an optical amplifier chip. FIG. 1 is a gain curve for a COTS booster optical amplifier.

Optical amplifier components can be provided in a standard 14-pin butterfly package with either single mode fiber (SMF) or polarization maintain fiber (PMF) pigtails, which can be terminated with any fixed connection (FC) connector such as an angled physical connection (FC/APC) connector. Optional polarization-maintaining isolators can be provided at the input, output, or both. In certain embodiments, the gain chip assembly includes a wavelength dependent reflector as a reflective surface of the optical amplifier, such as a mirror or one or more facets of the gain medium.

Figure 2:
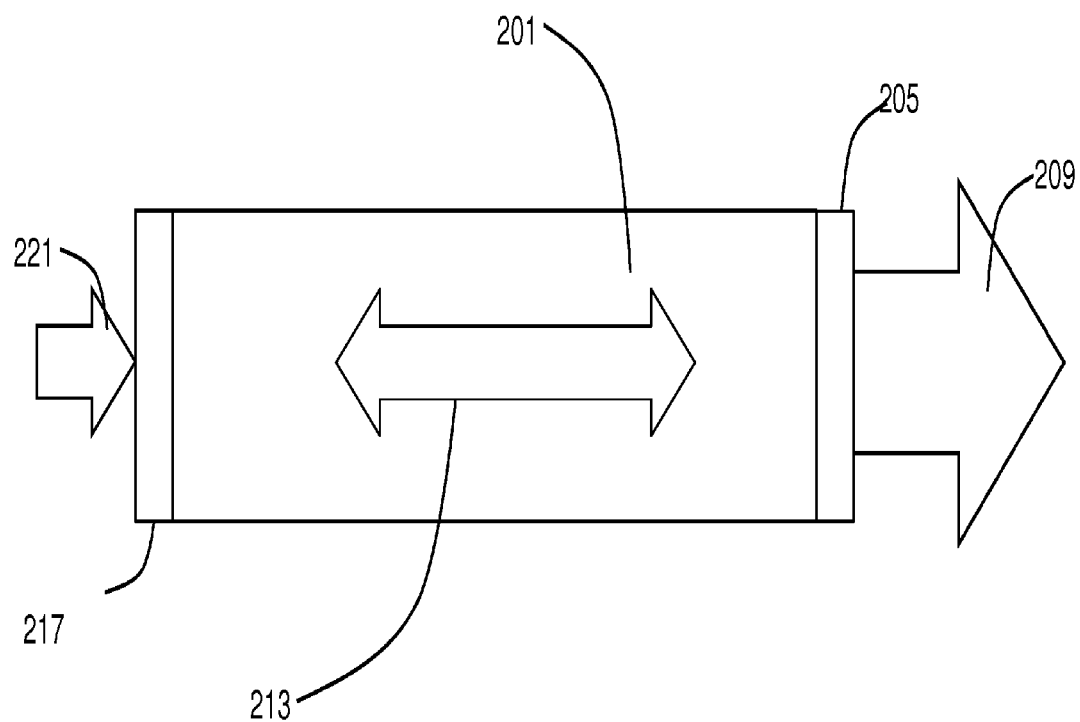
FIG. 2 is a diagram of a laser.

A laser generally is an optical amplifier in which the gain medium is positioned within an optical resonator (i.e., an optical cavity) as diagrammed in FIG. 2. In certain embodiments, an optical resonator is an arrangement of mirrors that forms a standing wave cavity resonator for light waves, e.g., a pair of mirrors on opposite ends of the gain medium and facing each other. The pair of mirrors includes a high reflector 217 and output coupler 205 surrounding the gain medium 201. Incident light 221 reflects between the mirrors creating standing wave 213. Some light is emitted as a laser beam 209. Where laser light is desired, the gain medium is positioned in an optical cavity. The optical cavity confines light in the gain medium, thereby feeding it amplified light back through the gain medium allowing it to be amplified again. Input light resonates between the mirrors while being re-amplified by the gain medium until the lasing threshold is surpassed and laser light is produced. This results in a positive feedback cycle tending to increase the gain G of the optical amplifier.

In a laser, one of the mirrors of the optical cavity is generally known as the high reflector while the other is the output coupler. Typically, the output coupler is partially transparent and emits the output laser beam. In certain embodiments, the invention provides a wavelength dependent reflector as a reflective surface with laser, such as one of the mirrors (e.g., the output coupler) or one of the facets of the gain medium.

A laser can be provided, for example, as a COTS component in a 14-pin butterfly package with either SMF or PMF pigtails. One such exemplary laser is the PowerPure 1998 PLM, a 980 nm pump laser module with Bragg grating available from Avanex Corporation (Fremont, Calif.).

In certain embodiments, a gain component such as an optical amplifier or a laser amplifies light in a frequency-specific manner. A gain component includes a gain medium having a gain coefficient g (gain per unit length) that is a function of the optical frequency of the incident signal w. The gain coefficient at a given frequency $g(\omega)$ is given by equation 3:

$$g(\omega)=g_0/(1+(\omega-\omega_0)^2 T^2+P/Ps) \qquad (3)$$

where $g_0$ is the peak gain of the medium, P is the optical power of the signal being amplified, Ps is the saturation power of the gain medium, $\omega_0$ is an atomic transition frequency of the medium, and T is a dipole relaxation time. Where incident light has a frequency $\omega$, a gain medium has a gain coefficient $g(\omega)$ and gain is given by Equation 4:

$$G(\omega)=\exp[g(\omega)L] \qquad (4)$$

where L is a length of the gain medium.

The power of amplified light at a distance z from the input end of a gain medium is given by Equation 5:

$$P(z)=P_{in}\exp(gz) \qquad (5)$$

Gain coefficient g has an inverse square relationship to $(\omega-\omega_0)$ (see Equation 3) and power P(z) is exponentially related to gain coefficient g. Thus, the gain of a gain medium is higher for optical frequencies w closer to $\omega_0$. FIG. 8 shows gain as a function of wavelength for a typical gain medium. As shown by the peak of the gain curve, the gain medium has a "peak gain."

If light of various wavelengths is amplified by the medium (at powers well below the saturation power Ps of the gain medium), light having a wavelength at or near the peak gain will be amplified to a greater degree than light having a wavelength not at or near the peak gain.

For any wavelength of light, if the gain is greater than the loss, lasing can result in which the light is emitted as a laser beam. The conditions at which gain equals loss is the lasing threshold for a frequency of light. The lasing threshold is lowest at the peak gain and light having a wavelength at the peak gain is more readily and more robustly amplified than at other wavelengths. Consequently, the gain medium most readily lases light at the peak gain.

Unintentional lasing is known as parasitic lasing. If light transmitted through the medium has sufficient power, wavelengths near the peak gain will cross the lasing threshold, causing lasing. This parasitic lasing leaches power from the system, reduces coherence length of signal light, and introduces noise into the signal. Due to the shape of the gain curve in a typical gain medium, parasitic lasing is problematic near the peak gain.

Devices and methods of the invention mitigate parasitic lasing and improve image quality. In one embodiment, systems and methods of the invention mitigate parasitic lasing by optimizing the time required to reach amplified light of a desired wavelength. Accordingly, undesired wavelengths have less opportunity to become amplified and also surpass the lasing threshold. In addition, image quality is also improved by reducing the time necessary to reach a desired wavelength.

In certain aspects, the gain component produces new infrared light from incident light delivered by a filter module in optical connection to the gain component. Preferably, the reflector is an output coupler and the gain component is a semiconductor optical amplifier. Systems of the invention further include any other compatible component known in the art. Exemplary components include interferometers, couplers/splitters, controllers, and any other device known in the art. Systems of the invention may include input and output mechanisms, such as an output mechanism configured to be coupled to a fiber optic interferometer or other imaging device. An optical system may include a controller component. For example, systems can include the LDC1300 butterfly LD/TEC controller from Thorlabs (Newton, N.J.). The LD/TEC controller and mount allows a system to be controlled by a computer. In certain embodiments, optical systems are integrated into an optical networking platform such as the Cisco ONS 15500 Dense Wave Division Multiplexer.

In certain embodiments, the system includes an interferometer such as a fiber optic interferometer. An interferometer, generally, is an instrument used to interfere waves and measure the interference. Interferometry includes extracting information from superimposed, interfering waves.

As encompassed by the invention, a portion of the amplified light leaving the gain chip assembly is directed back into the assembly. In certain aspects, this re-direction is accomplished using a partial mirror. Mirrors typically reflect uniformly over a broad spectral range. In contrast, partial mirrors work at off-normal angles of incidence, thereby reflecting only a portion of the light while transmitting the remainder. In certain aspects, a partial mirror is appropriately positioned outside the gain chip assembly so that when light leaves the assembly, it is reflected by the partial mirror back into the assembly. Accordingly, light is amplified a second time upon re-entering the gain chip assembly.

Any material suitable for antireflective coating may be used to construct the partial mirror. Exemplary materials include metals such as aluminum, silver, or gold or compounds such as magnesium fluoride. Additional exemplary coated materials are sold under the trademark HEBBAR by CVI Melles Griot (Albuquerque, N. Mex.).

Coatings of the desired thickness can be fabricated by any method known in the art including, for example, vacuum deposition, electric bombardment vaporization, plasma ion-assisted deposition (PIAD), carbon vapor deposition, plasma vapor deposition, and related techniques. In vacuum deposition, a substrate is put in a vacuum chamber along with a metal crucible holding the coating substance. A high current (e.g., 100 A) is passed through the coating material, vaporizing it. Due to the vacuum, the vaporized material disperses to the material to be coated.

In certain aspects, the filter and gain chip assembly are connected with optical fibers, such that light transmitted from the filter travels through the optical fiber to the gain chip assembly and from the gain chip assembly back into the filter. In certain aspects of the invention, one optical fiber transmits light from the filter to the gain chip assembly, while a second optical fiber transmits light from the gain chip assembly back to the filter.

Optical fibers are flexible, transparent fibers able to transmit light from one end of the fiber to the other. Optical fibers can be prepared from glass (silica) or from a variety of plastic polymers. Optical fibers usually include a transparent core surrounded by a transparent cladding material with a lower index of refraction. Light is kept in the core by total internal reflection, which causes the fiber to act as a waveguide or "light pipe."

Any type of optical fiber is useful for practicing the invention, including multi-mode fibers (MMF) and single-mode fibers (SMF). MMF fibers support many propogation paths or transverse modes while SMF fibers support only a single mode. MMF fibers usually have wider core diameter than SMF fibers, and are used for short-distance communication links and for applications where high power must be transmitted. SMF fibers are often used for communication links longer than 1000 meters. Assemblies of multiple fibers can also be prepared in wrapped bundles, which are often used for imaging procedures. The selection of the appropriate fibers and their connection to the various components described herein is within the skill of the art. For example, MMF fibers having a wavelength range of 400-2400 nm are available from Thorlabs (Item No. AFS50/125Y).

Further embodiments of the invention include an optical circulator for redirecting light among the various components encompassed by the invention. For example, light can travel from the filter to the circulator through an optical fiber connecting both the filter and the circulator. The light can then travel from the circulator to the gain chip assembly and back again via a separate optical fiber connecting the circulator to the gain chip assembly.

An optical circulator is a special fiber-optic component that can be used to separate optical signals that travel in different directions in an optical fiber. Optical circulators are typically three-port devices, configured such that light entering any port exits from the next. This means that if light enters port 1, it is emitted from port 2, but if some of the emitted light is reflected back to the circulator, it does not come out of port 1, but instead exits from port 3. In this sense, fiber optic circulators act as signal routers, transmitting light from an input fiber at a first port to an output fiber at a second port, but directing light that returns along the output fiber to a third port. Circulators protect the input fiber from return power, but also allow the rejected light to be employed. The selection of the appropriate circulators and their connection to the various components described herein is within the skill of the art. For example, optical circulators having a wavelength range of 1525-1610 nm are available from Thorlabs, Inc (Item No. 6015-3-APC).

As encompassed by the invention, light from the filter enters the circulator at a first port, and exits the circulator at a second port, which is connected to the gain chip assembly. When the light amplified in the gain chip assembly reaches the lasing threshold, light is emitted from the gain chip assembly. The emitted light meets a partial mirror outside the gain chip assembly, whereupon a portion of the amplified light is reflected back into the assembly. The amplified light is amplified for a second time in the gain chip assembly. This re-amplified light travels back to the circulator, entering the circulator at the second port. The re-amplified light then exits the circulator out the third port, whereupon the re-amplified light travels back to the filter and the whole process can begin again.

The present invention can operate as a light source for a variety of uses, including imaging applications. In certain aspects, the unreflected portion of the light leaving the gain chip assembly is directed to an optical tomography (OCT) system. Systems and methods of the invention are particularly amenable for use in OCT as the provided systems and methods can improve image quality and reduce the incidence of parasitic lasing.

Measuring a phase change in one of two beams from a coherent light is employed in optical coherence tomography. Commercially available OCT systems are employed in diverse applications, including art conservation and diagnostic medicine, e.g., ophthalmology. Recently, it has also begun to be used in interventional cardiology to help diagnose coronary heart disease. OCT systems and methods are described in U.S. Patent Application Nos. 2011/0152771; 2010/0220334; 2009/0043191; 2008/0291463; and 2008/0180683, the contents of which are hereby incorporated by reference in their entirety.

Various lumen of biological structures may be imaged with the aforementioned imaging technologies in addition to blood vessels, including, but not limited to, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus, and fallopian tubes, structures of the urinary tract including urinary collecting ducts, renal tubules, ureter, bladder, and structures of the head, neck, and pulmonary system including sinuses, parotid, trachea, bronchi, and lungs.

In OCT, a light source delivers a beam of light to an imaging device to image target tissue. Within the light source is an optical amplifier and an tunable filter that allows that allows a user to select a wavelength of light to be amplified. Wavelengths commonly used in medical applications include near-infrared light, for example, 800 nm for shallow, high-resolution scans or 1700 nm for deep scans.

Generally, there are two types of OCT systems, common beam path systems and differential beam path systems, which differ from each other based upon the optical layout of the systems. A common beam path system sends all produced light through a single optical fiber to generate a reference signal and a sample signal, whereupon a differential beam path system splits the produced light such that a portion of the light is directed to the sample and the other portion is directed to a reference surface. The reflected light from the sample is recombined with the signal from the reference surface of detection. Common beam path interferometers are further described in, for example, U.S. Pat. Nos. 7,999,938; 7,995,210; and 7,787,127, the contents of which are incorporated by reference herein in its entirety.

In a differential beam path system, amplified light from a light source is inputted into an interferometer with a portion of light directed to a sample and the other portion directed to a reference surface. A distal end of an optical fiber is interfaced with a catheter for interrogation of the target tissue during a catheterization procedure. The reflected light from the tissue is recombined with the signal from the reference surface, forming interference fringes that allow precise depth-resolved imaging of the target tissue on a micron scale. Exemplary differential beam path interferometers are further described in, for example, U.S. Pat. Nos. 6,134,003; and 6,421,164, the contents of which are incorporated by reference herein in its entirety.

Figure 4:
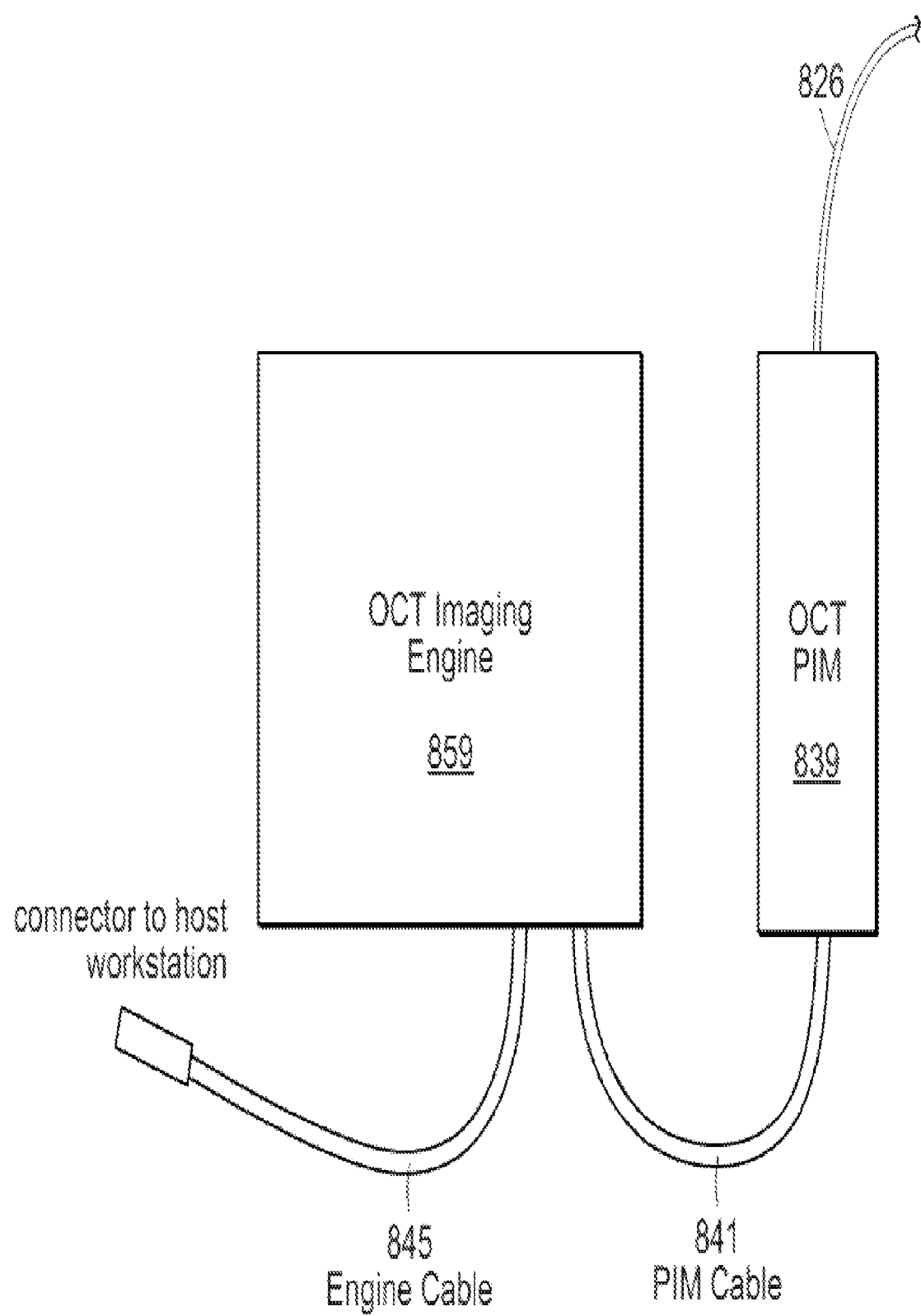
FIG. 4 is a schematic of an optical coherence tomography (OCT) system for use with systems and methods of the invention.

In certain embodiments, the invention can be used in conjunction with a differential beam path OCT system with intravascular imaging capability as illustrated in FIG. 4. In these embodiments, systems and methods of the invention can be used to provide a light source of narrow wavelength light. For intravascular imaging, a light beam is delivered to the vessel lumen via a fiber-optic based imaging catheter 826. The imaging catheter is connected through hardware to software on a host workstation. The hardware includes an imaging engine 859 and a handheld patient interface module (PIM) 839 that includes user controls. The proximal end of the imaging catheter is connected to PIM 839, which is connected to an imaging engine as shown in FIG. 4.

Figure 5:
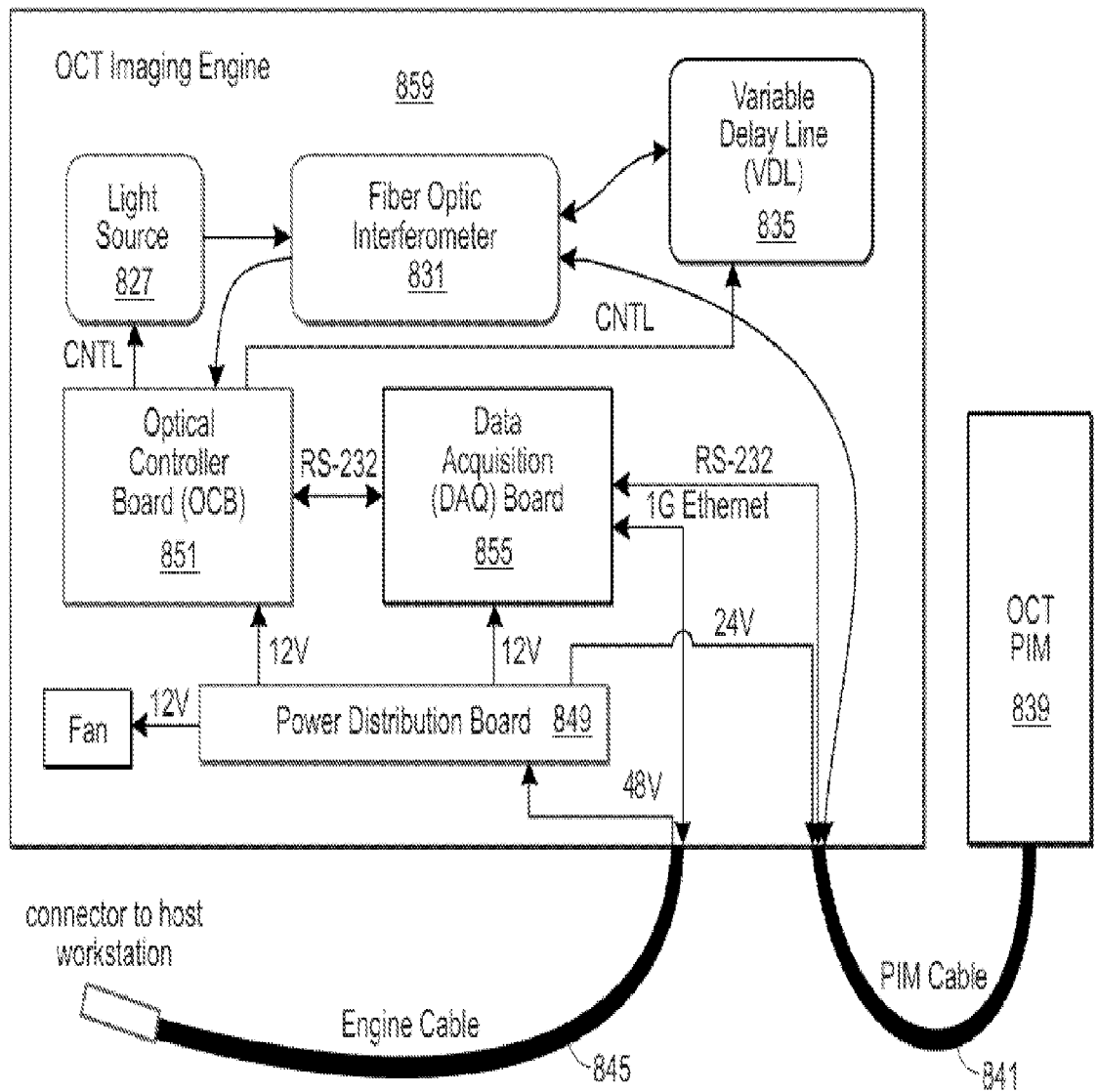
FIG. 5 is a schematic diagram of the imaging engine of an OCT system.

As shown in FIG. 5, the imaging engine 859 (e.g., bedside unit) houses a power supply 849, a light source 827 in accordance with the methods and systems described herein, interferometer 931, and variable delay line 835 as well as a data acquisition (DAQ) board 855 and optical controller board (OCB) 854. A PIM cable 841 connects the imaging engine 859 to the PIM 839 and an engine cable 845 connects the imaging engine 859 to the host workstation.

Figure 6:
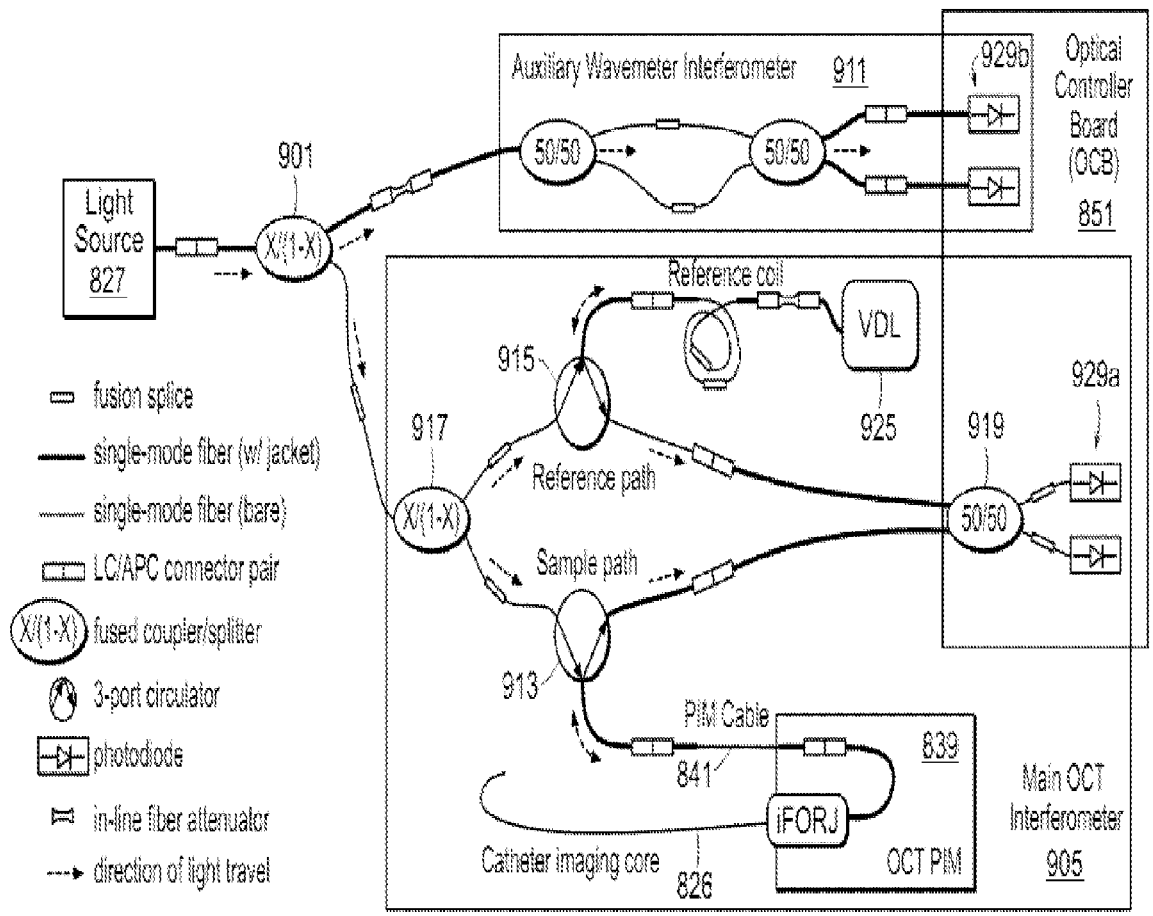
FIG. 6 is a diagram of a light path in an OCT system.

FIG. 6 shows the light path in an exemplary embodiment of the invention. Light for image capture originates within the light source 827. This light is split between an OCT interferometer 905 and an auxiliary interferometer 911. The OCT interferometer generates the OCT image signal and the auxiliary, or "clock" interferometer characterizes the wavelength tuning nonlinearity in the light source and generates a digitizer sample clock.

In certain embodiments, each interferometer is configured in a Mach-Zehnder layout and uses single mode fiber optics to guide the light. Fibers are connected via LC/APC connectors or protected fusion splices. By controlling the split ratio between the OCT and auxiliary interferometers with splitter 901, the optical power in the auxiliary interferometer is controlled to optimize the signal in the auxiliary interferometer. Within the auxiliary interferometer, light is split and recombined by a pair of 50/50 coupler/splitters.

Light directed to the main OCT interferometer is also split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter 826 where the image is captured.

Figure 7:
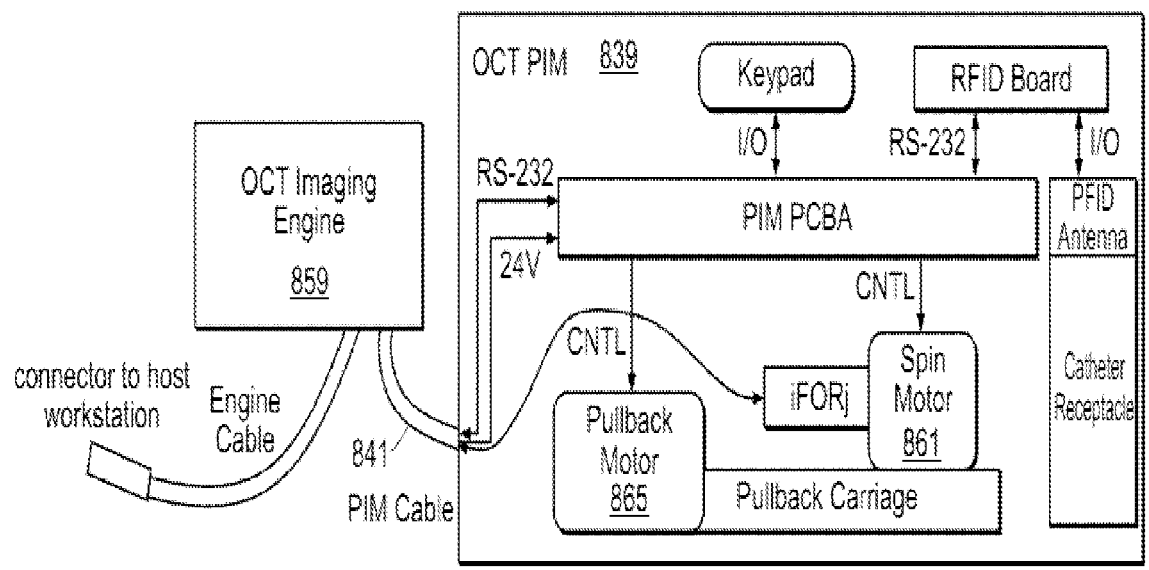
FIG. 7 shows the organization of a patient interface module in an OCT system.

Typical intravascular OCT involves introducing the imaging catheter into a patients' target vessel using standard interventional techniques and tools such as a guidewire, guide catheter, and angiography system. When operation is triggered from the PIM or control console, the imaging core of the catheter rotates while collecting image data that it delivers to the console screen. Rotation is driven by spin motor 861 while translation is driven by pullback motor 865, as shown in FIG. 7. Blood in the vessel is temporarily flushed with a clear solution while a motor translates the catheter longitudinally through the vessel.

In certain embodiments, the imaging catheter has a crossing profile of 2.4 F (0.8 mm) and transmits focused OCT imaging light to and from the vessel of interest. Embedded microprocessors running firmware in both the PIM and the imaging engine control the system. The imaging catheter includes a rotating and longitudinally-translating inner core contained within an outer sheath. Using light provided by the imaging engine, the inner core detects reflected light. This reflected light is then transmitted along a sample path to be recombined with the light from the reference path.

A variable delay line (VDL) 925 on the reference path uses an adjustable fiber coil to match the length of the reference path 915 to the length of the sample path 913. The reference path length is adjusted by translating a mirror on a lead screw based translation stage that is actuated electromechanically by a small stepper motor. The free-space optical beam on the inside of the VDL 925 experiences more delay as the mirror moves away from the fixed input/output fiber. Stepper movement is under firmware/software control.

Light from the reference path is combined with light from the sample path. This light is split into orthogonal polarization states, resulting in RF-band polarization-diverse temporal interference fringe signals. The interference fringe signals are converted to photocurrents using PIM photodiodes 929a and 929b on the OCG as shown in FIG. 6. The interfering, polarization splitting, and detection steps are performed by a polarization diversity module (PDM) on the OCB. Signal from the OCB is sent to the DAQ 855, shown in FIG. 5. The DAQ includes a digital signal processing (DSP) microprocessor and a field programmable gate array (FPGA) to digitize signals and communicate with the host work station and the PIM. The FPGA converts raw optical signals into meaningful OCT images. The DAQ also compresses data as necessary to reduce image transfer bandwidth to 1 Gbps.

In certain embodiments, the invention provides a light source for OCT including a filter, a gain chip assembly comprising a gain medium, and a partially reflecting mirror. The components are configured such that light passes from the filter to the gain chip assembly and a portion of the light is reflected by the partial mirror back through the gain chip assembly before the light passes again through the filter.

Any filter known in the art compatible with the invention may be used, including, for example, a tunable filter. The filter is included to deliver light of a specified wavelength into an optical amplifier. The filter typically has a peak reflectivity and a background reflectivity. In some embodiments, the system includes a commercial off-the-shelf (COTS) filter. One exemplary filter for use with the use with the invention is filter module TFM-687 by Axsun technologies, Inc. (Billerica, Mass.). An exemplary tunable optical filter exhibits 20% reflectivity and 29 dB contrast ratio.

Any optical amplifier or laser known in the art and compatible with the invention may be used as the gain component including, for example, a semiconductor optical amplifier. The amplifier amplifies the light to a sufficient output power for imaging by OCT. The amplifier typically has a semiconductor gain medium and an optical cavity. In some embodiments, a system includes a COTS amplifier. One exemplary optical amplifier for use with the invention is booster optical amplifier serial number BOA1130S, BOA1130P, or BOA-8702-11820.4.B01 from Thorlabs (Newton, N.J.). An exemplary optical amplifier has a center wavelength of 1285 nm and a small signal gain of 30 dB with a chip length of 1.5 mm.

A mirror can be coated with wavelength dependent material. Suitable materials are available from Unioriental Optics co., Ltd (Zhong Guan Cun Science Park, Beijing, China).

Figure 3:
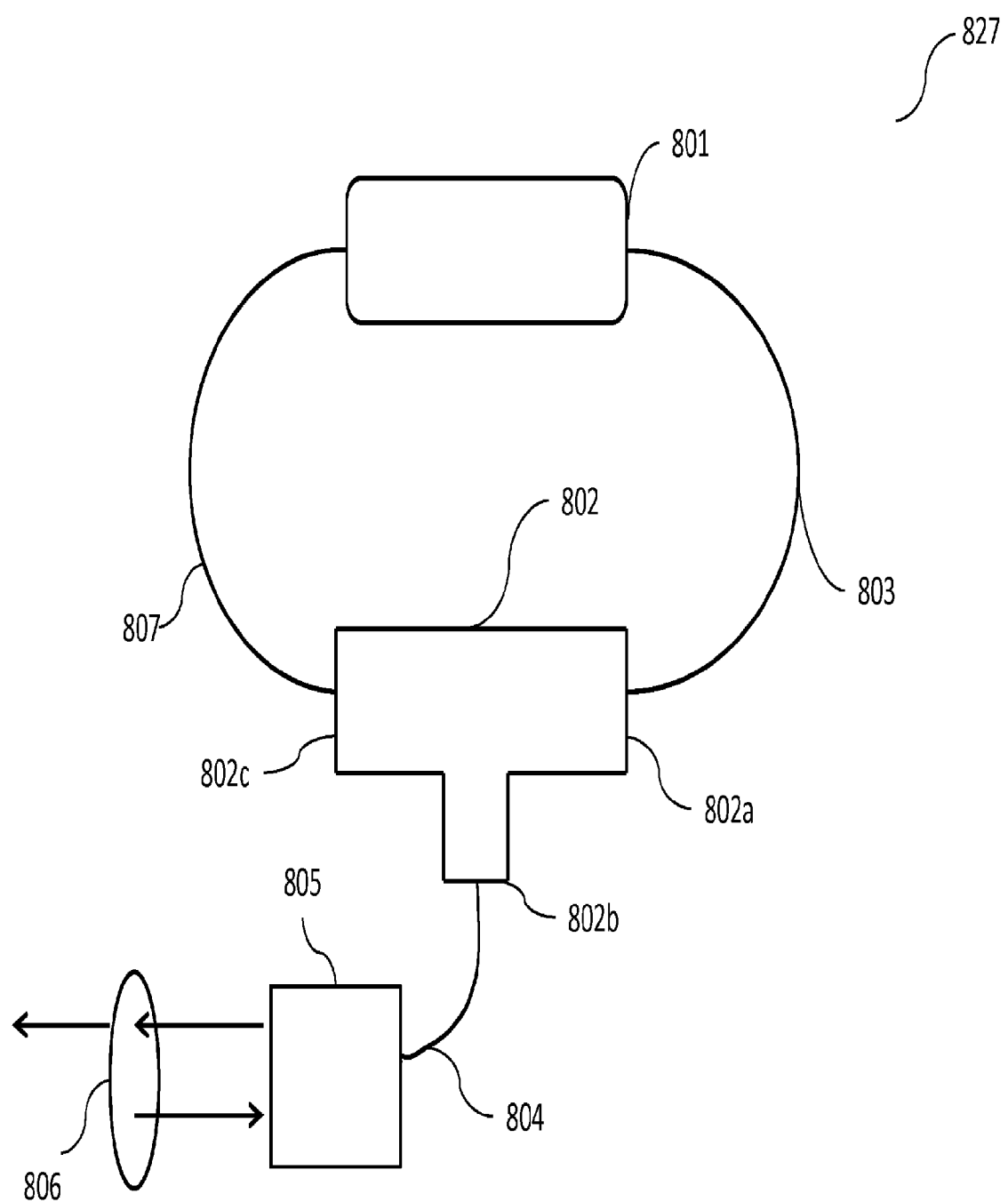
FIG. 3 schematically depicts a system of the invention, according to certain embodiments.

In certain embodiments, the invention provides a light source that emits narrow wavelength light for OCT systems like those shown in FIGS. 4 and 5. Exemplary components of light source 827 are illustrated schematically in FIG. 3. Tunable optical filter 801 provides light to an optical circulator 802 at a first port 802a via a first optical fiber 803. The light exits the circulator 802 at a second port 802b and travels through a second optical fiber 804 to a gain chip assembly 805. The operation of the gain chip assembly 805 has already been presented schematically in FIG. 2. When the light amplified in the gain chip assembly 805 reaches the lasing threshold, light is emitted from the assembly 805. The emitted light meets a partial mirror 806 outside the gain chip assembly 805, whereupon a portion of the light is reflected back into the assembly 805. The amplified light is amplified for a second time in the gain chip assembly 805. This re-amplified light travels back to the circulator 802 through the second optical fiber 804, entering the circulator 802 at the second port 802b. The re-amplified light then exits the circulator 802 out the third port 802c, whereupon the re-amplified light travels back to the filter 801 via a third optical fiber 807 and the whole process can begin again. Accordingly, systems and methods are able to produce narrow emissions of light faster than conventional methods by transmitting light through a filter and passing a portion of the filtered light through the gain chip assembly at least two times before that portion of filtered light passes again through the filter. This reduction in time to achieve the desired wavelength results in improved image quality and reduces the incidence of parasitic lasing.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of narrowing a wavelength emission of light, the method comprising:
   transmitting light through a filter in a first direction;
   sending the light from the filter through an optical circulator to a gain medium in a gain chip assembly a first time;
   reflecting a portion of the light leaving the gain chip assembly back through the gain medium in the gain chip assembly a second time and back into the optical circulator;
   sending the reflected portion of the light from the gain chip assembly back through the filter again in the first direction;
   sending the reflected, filtered portion of the light through the optical circulator to the gain medium in the gain chip assembly for a third time;
   directing an unreflected portion of the light leaving the gain chip assembly, after the first time and after the third time, to an optical coherence tomography (OCT) system with intravascular imaging capability, such that the OCT system receives light that has passed twice through the filter and three times through the gain chip assembly.

2. The method of claim 1, wherein reflecting is accomplished using a partial mirror.

3. The method according to claim 1, wherein the filter is a tunable filter.

4. The method of claim 3, wherein the filter is a voltage-controlled optical attenuator.

5. The method of claim 1, wherein the gain medium is a semiconductor.

6. A system for narrowing a wavelength emission of light, the system comprising:
   a filter;
   an optical circulator;
   a gain chip assembly comprising a gain medium,
   a partially reflecting mirror; the system being configured such that light passes from the filter in a first direction, through the optical circulator, to the gain chip assembly and a portion of the light is reflected by the partial mirror back through the gain chip assembly and back through the optical circulator where the light is directed through the filter again in the first direction, through the optical circulator, and back through the gain chip assembly and to the partial mirror again such that light reflected by the partial mirror is filtered once and passes through the gain chip assembly twice each time before reaching the partial mirror again;
   an optical coherence tomography (OCT) system with intravascular imaging capability wherein the OCT system is configured to receive an unreflected portion of the light that passes through the gain chip assembly.

7. The system according to claim 6, wherein the filter is a tunable filter.

8. The system of claim 7, wherein the filter is a voltage-controlled optical attenuator.

9. The system of claim 8, wherein the gain medium is a semiconductor.

* * * * *